United States Patent
Krysan et al.

(10) Patent No.: US 6,358,690 B1
(45) Date of Patent: Mar. 19, 2002

(54) METHOD FOR RAPIDLY IDENTIFYING DELETION MUTATIONS

(75) Inventors: Patrick John Krysan; Michael Richard Sussman, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/665,995

(22) Filed: Sep. 20, 2000

(51) Int. Cl.[7] .............................. C12Q 1/68; C12P 19/34
(52) U.S. Cl. ............................................ 435/6; 435/91.2
(58) Field of Search ..................................... 435/6, 91.2

(56) References Cited

PUBLICATIONS

Wittwer, C.T. et al., "Rapid Cycle DNA Amplification: Time and Temperature Optimization", BioTechniques vol. 10, pp. 76–83 (1991).*

Yoshino M. et al., "Detection of terminal deletions in barley chromosomes by the PCR–based method", Genes and Genet. Syst. vol. 73, pp. 163–166 (1998).*

Roux, K.H., "Optimization and Troubleshooting in PCR", pp. 53–62, PCR Primer: A laboratory Manual, ed. Dieffenbach C.W. et al., Cold Spring Harbor Laboratory Press (1995).*

Kretz K. et al., "Cycle Sequencing", pp. 527–536, PCR Primer: A laboratory Manual, ed. Dieffenbach C.W. et al., Cold Spring Harbor Laboratory Press (1995).*

* cited by examiner

Primary Examiner—Kenneth R. Horlick
Assistant Examiner—Teresa Strzelecka
(74) Attorney, Agent, or Firm—Quarles & Brady LLP

(57) ABSTRACT

A method is described for the detection of a rare deletion mutant allele in a population of wild-type individuals. DNA samples from the individuals are subjected to a modified form of polymerase chain reaction (PCR) which favors the replication of truncated DNA strands over the synthesis of wild-type full length strands. The preferred way to bias the process toward the synthesis of truncated DNA strands is by limiting the extension step in the PCR reaction protocol. This process permits the convenient detection of a deletion mutant allele from a population of 1000 wild type individuals with the full length allele.

8 Claims, No Drawings

METHOD FOR RAPIDLY IDENTIFYING DELETION MUTATIONS

CROSS-REFERENCE TO RELATED APPLICATIONS

Not applicable.

STATEMENT REGARDING FEDERALLY SPONSORED RESEARCH OR DEVELOPMENT

To be determined.

BACKGROUND OF THE INVENTION

One of the objectives of much genetic research is to identify the genes responsible for selected phenotypic traits in individuals. While much effort is being undertaken to develop genomic information from a large number of organisms, often the information about the function of a gene is more important than information as to the sequence of the gene itself. One way in which the function of individual genes is studied is to look for mutated versions of the gene of interest. Sometimes the search for mutated versions of a gene and the study of the mutated genes is referred to as "reverse genetics." If one finds a gene which is mutated so as to render the mutated gene inoperative, one can discern what phenotypic change has been made to the organism that renders it different from organisms not carrying the mutated version of the gene. Such studies can often lead to insightful information about the function of the gene which has the mutation.

Various strategies have been developed for using reverse genetics to study the functioning of genes in the model plant species *Arabidopsis thaliana*. For example, one laboratory at the University of Wisconsin has created a large population of Arabidopsis plant lines each of which has been transformed using the transferred-DNA (T-DNA) from the bacterium *Agrobacterium tumefaciens*, which has the native ability to transfer its T-DNA into the genome of a plant cell. Since the mechanism for DNA transfer operated by Agrobacterium results in a random insertion of the transferred DNA into the plant genome, the use of the Agrobacterium transformation technique results in large populations of plants each of which has a potentially disruptive insert at a different place within the plant genome. The problem then becomes to identify the particular gene which has been disrupted within each of the plants and to determine what the function of the gene might have been prior to disruption.

Another technique for introducing mutations into genes in an individual species under study, as such as a plant, is to introduce transposable elements into the genome of the organism. Various transposable elements are known in plants and many are known to be immobilized in Arabidopsis plants. A transposable element transports itself within the genome to insert itself randomly within the genome of the plant. Such random insertion mutations also could help identify the function of genes by disrupting the function of those genes and permitting the disruption to be observed at a phenotypic level.

Another method used to produce random mutations in the genome of various species, such as plants, is to expose the tissues of the plant to ionizing radiation. Ionizing radiation is known to produce deletion mutations in the genome of many plant species. The deletions created range in size from less to 1 kilobase to large chromosomal scale deletions that remove entire arms of chromosomes. Inducing such deletions in the genome of a plant is as simple as exposing a bag of seeds to the ionizing radiation. The radiated seeds can then be planted and each resulting plant carries a different deletion mutation. By collecting the seeds of the resultant plants one can easily generate a large population of plants that carry deletion mutations throughout the entire genome. No special transformation or transposon protocols are needed, and one is limited only by the amount of space available to grow the plants.

Whichever method of mutation creation is used, the problem still becomes to rapidly localize the rare organisms that carry a mutant version of the particular gene of interest. Thus what is needed is a method for rapidly identifying relatively rare deletion mutations within a population of organisms, such as a plant.

BRIEF SUMMARY OF THE INVENTION

The present invention is summarized in that a technique based on a polymerase chain reaction (PCR) has been developed that permits the rapid and efficient characterization of deletion mutants in individual organisms.

The present invention is also summarized in a method that allows one to identify individual *Arabidopsis thaliana* plants which contain a single deletion mutation in their genome, the deletion resulting in a functional mutation of a gene of interest.

Other objects, advantages and features of the present invention will become apparent from the following specification.

BRIEF DESCRIPTION OF THE SEVERAL VIEWS OF THE DRAWINGS

Not applicable.

DETAILED DESCRIPTION OF THE INVENTION

The method described here was developed for a situation in which one individual in a population of individuals of that species carries a deletion mutation in a particular gene, the function of which is sought to be studied. The sequence of the gene is known, and enough random deletion mutants have been made that the statistical likelihood is high that an individual exists in the population with a deletion mutation in the gene of interest, but the identity of that particular individual is not known. This method provides a very practical and efficient method that may be used to identify the individual with a deletion mutation in the desired locus.

The method is based on the polymerase chain reaction, or PCR, which is now a standard protocol of molecular biology and genetic laboratories. In a standard PCR reaction, the object is to amplify, or replicate exponentially copies of a particular sequence of a target DNA sequence possibly present in a sample. The PCR reaction in performed in a series of rounds, and in each round there are steps of denaturing, annealing and extending. In the denaturing step, the double stranded DNA is heated so as to denature the double stranded DNA so that it becomes single stranded. In the annealing step, the temperature is lowered so that conditions permit the annealing of specially made primers, which have sequences selected to bind to the target sequence, to the target DNA forming partially double stranded complexes. Then in the extension step, a DNA polymerase replicates the complement of the target strand by beginning at the double stranded complex of the primer and the target and extending the sequence of the primer using target sequence as a template. The product of each round of replication becomes a template for the next round. In the presence of excess primer, the target sequence is exponentially amplified. These three steps of denaturing, annealing, and extension are conducted repeatedly, each amplifying the complement of the target sequence, if it is present at all, until sufficient amplified DNA is made to be detectable by some detection procedure. In normal PCR, the object is to amplify the full length target sequence and thus the parameters of the process are normally arranged so as to maximize the yield of full length product made.

In the method of the present invention, the object is not to make full length target strands but to find, in essence, shorter sequences. The PCR process is adjusted by manipulating the three basic steps so that the shorter target sequences, representing the deletion mutations, are selectively amplified in preference over the full length sequences. This can be done most conveniently by limiting the time of the extension step in the process. Making this modification to standard PCR results in a process which selectively favors the amplification of shorter DNA species that still bind to the primers. In other words, this modified form of PCR reaction results in selective amplification of deletion mutant forms of native genes.

It is envisioned that this process will be used with pooled DNA from many individuals, for reasons of practical convenience. To screen large populations of individuals for presence of a desired deletion mutation, DNA from the individuals is obtained and processed in large pools, each pool containing the DNA from thousands of individuals. Then the pools can be tested for the presence of the deletion mutation in that pool. For any pool in which a deletion mutation is found, the pool can be divided into sub-pools which can then be retested. This process can be repeated until the individual organism with the deletion mutant allele is identified. Thus, for reasons of practicality, it is desired that the process can detect one mutant shortened allele in a pool of 1000 copies of the wild-type full length alleles.

Tables 1 and 2 illustrate a comparison of a standard PCR reaction with the modified reaction for deletion mutant amplification. Both reaction use primers selected to bind to the target sequence and use the steps of denaturing, annealing and extension repeated cyclically. In the standard PCR reaction of Table 1 the denaturing step is conducted at 94° C. for a time of 10 seconds. Then the temperature of the reaction mixture is lowered to 65° C. for the annealing step which is conducted for 30 seconds. Lastly, the extension step is conducted at 72° C. for a time period of two minutes, normally the longest step in the reaction by far. The temperatures of the three steps are normally selected with the optimum for each object in mind. The denaturing step and the annealing step requires the solution to be adjusted to temperatures consisted with only single or double stranded DNA species being present in the mix. The temperature of the extension step is chosen for the optimum performance of the DNA polymerase. The time periods of the reaction steps are chosen so that the reaction taking place in each step can be completed. The long time period of the extension step is necessary to ensure that full length replications of the entire target sequence can be constructed by the DNA polymerase.

TABLE 1

| A | 94° C. | 10 seconds |
| B | 65° C. | 30 seconds |
| C | 72° C. | 2 minutes |

Steps A, B, and C are repeated sequentially 30 times.

TABLE 2

| A | 94° C. | 10 seconds |
| B | 65° C. | 1 second |
| C | 72° C. | 10 seconds |

Steps A, B, and C are repeated sequentially 35 times.

In the amplification process for deletion mutant genes, the process is altered to favor the production of the shortened amplified species. This is illustrated in Table 2. The denaturing time is left at 10 seconds at 94° C. The time for the annealing step is compressed to 1 second at 65° C. Most critically, the time for the extension step is reduced to 10 seconds, still at 72° C. In this way, there is sufficient time period for shorter target strands to be replicated by the DNA polymerase, but there will be insufficient time period for a population of full length target strand to be made.

In a modem molecular biology laboratory, PCR reactions are performed in devices known as thermocyclers. These instruments are programmed by the user to take a reaction mixture and subject that mixture to a series of different temperatures for preselected times so that defined reactions occur. All of the PCR reactions described here, both the conventional reactions and the deletion mutation enrichment reactions, can conveniently be performed in such thermocyclers programmed to provide the temperatures and times as suggested in this document. Also, unless stated otherwise, standard commercially available reagents for PCR reactions, including DNA polymerases and buffer, can be used in these reactions, and such reagents are commercially available from a number of manufacturers.

The altered PCR deletion enrichment procedure of Table 2, if applied to a mixture of DNA strands, some of which might contain a deletion mutation. The deletion mutant can be rare, perhaps 1 copy of a deletion mutation in amongst 1000 copies of a wild-type full length gene. Yet this process will selectively amplify or multiply only the deletion mutation version of the gene, not the native full length version. Thus by conducting pooled experiments, it becomes convenient to determine if a desired mutation has occurred in any of the individuals represented in large pools of DNA from many individuals. Once the existence of the deletion mutation in a pool is demonstrated, subsequent division of the pool and re-testing can lead to successful identification of the individual carrying the deletion mutation.

The time period for the extension step may need to be varied for different length deletions, and for different target DNA sequences, but the principle here is clear. It is possible to perform a PCR reaction process and manipulate the conditions to favor the multiplication of copies of gene which have deletion mutations in them in preference to full length genes without the deletion mutations. The extent to which the amplification of the deletion mutants is favored over the full length copies may vary somewhat in its magnitude depending on the parameters of the PCR process. At least the amplification of the deletion copy will be greater than the amplification of the non-mutant versions but often, as in the examples below, only the mutant version of the gene will amplified by the process.

Sometimes the amplification of the deletion mutant will not be sufficient in one PCR process to result in enough amplified DNA to be visible by a technique such as agarose gel electrophoresis. In such cases, it is possible and recommended to conduct a second round of PCR using primers nested inside the primers for the first reaction, but primers which will still bind to a mutant version of the target gene.

It has been found, as again shown in the examples below, that such a second round of PCR is useful to increase the number of copies of the mutant version of the target DNA sequence in order to make possible a visual indication that the mutant gene has been found.

There are also other ways to vary the PCR process to selectively favor the creation of copies of truncated genes in preference to full length genes. Temperature is another parameter which can be altered. If the time of the elongation step were not changed, but the temperature were reduced, the speed of the reaction could be slowed in a manner that is the equivalent of shortening the reaction time for the elongation reaction. The lowering of the temperature might allow for a broader range of times to be used in the extension reaction while still favoring the complete synthesis of deletion mutant over the longer wild type versions.

Another approach is to use dideoxynucleotides in the extension reactions. The chemical nature of dideoxynucleotides is such that they are recognized by DNA polymerases and are incorporated into growing DNA strands. However, once a dideoxynucleotide is incorporated into a growing DNA strand, the strand can grow no further since a new nucleotide cannot be added to the dideoxynucleotide. One could conduct the extension reaction with a mixture of normal nucleotides and dideoxynucleotides which would limit the length to which a daughter strand could grow, at least as a statistical matter. The more dilute the dideoxynucleotides were, the longer the strands could grow before they were terminated by the incorporation of dideoxynucleotide. By manipulating the ratio of normal to dideoxynucleotides, one could vary the length to which the growing DNA strands grow and thus favor the truncated strands over the longer ones. A DNA strand which is shorter than the average length of the terminated DNA strands would be favored using this strategy.

Yet another way to favor the synthesis of deletion mutations over full length genes would be to use a less efficient DNA polymerase. A DNA polymerase that was slower, had lower processivity, or which had less affinity for the template strand, would also favor the synthesis of shorter strands over longer ones. It might be possible to identify a DNA polymerase or a combination of polymerases or additives which results in a controllable bias toward shorter strands over longer ones.

But the preferred method of biasing the reaction toward shorter strands is to limit the time of the extension portion of the reaction. The preferred reaction is to use a temperature of about 72° C. and a time period of about 10 seconds. For the HY-4 example given below, good results were obtained using reaction times of between 7 and 14 seconds. If an extension time of longer than 14 seconds is used, the danger becomes that the deletion template may lose its competitive advantage over the wild-type templates, and the deletion product might not be detectable. Again, however, this parameter may need to be varied somewhat depending on the difference in length between the truncated template and the full-length template. The larger the gene of interest, the longer the extension time that should be used. It is possible to test empirically how long the time can be extended and still not result in large amounts of the wild-type DNA being replicated in the reaction.

All of these strategies have one common feature. They favor the synthesis in the extension step of a PCR reaction, of shorter daughter DNA strands over the synthesis of longer strands. Such favoring does not have to be absolute, it just must be sufficient so that detectable quantities of a rare deletion mutant can be favored so that its DNA becomes detectable in some fashion.

EXAMPLES

Arabidopsis HY-4 gene

To test this method, a conveniently available known and characterized deletion mutant was first used. The mutation selected was a mutation in the HY-4 gene which had been studied by Bruggemann et al., *Plant Jour.* 10(4):755–760 (1999) And was known to be about 500 bp in size. This deletion mutation was originally isolated by screening for a phenotype of plants showing etiolated growth characteristics. The mutation was created by irradiating a pool of Arabidopsis seeds with fast neutron radiation, such seeds being available from Lehle Seeds. The seeds are sold as batches of seed collected from pools derived from 1,500 parental lines per pool. It was possible to order a seed pool from Lehle that was known to contain a 500 bp deletion in the HY-4 locus mixed in a packet with seeds derived from of 1,499 other individuals with the wild-type native gene form.

DNA primers which would amplify the HY-4 gene in wild type Arabidopsis were selected. Tests were first conducted to verify that the primers would, in fact, amplify the native gene in a standard PCR protocol. Then the parameters of the PCR reaction were modified in stages to examine which conditions would favor the amplification of the deletion mutations of the target gene. It was found that shortening the extension time was the most effective change to the parameters that could be made to achieve this objective. Using primers effective under standard condition to amplify the full length gene, extension time periods of 30 seconds, 20 seconds, 15 seconds and 10 seconds were used. The reactions with the 30 second extension times produced product strands that included an abundant representation of the wild-type gene. Reducing the extension time to 20 or 15 seconds reduced the amount of wild-type full length gene product from the amplification process, but did not produce an amount of the deletion mutant allele that was apparent compared to the still remaining full length wild-type product. When the extension time was reduced to 10 seconds, no PCR product was visible on an agarose gel.

To determine if the deletion mutant was amplified, even though at less than easily visible levels, a second round of PCR was conducted using nested primers which would correspond to sequences inside of the PCR product from the first round. The reaction mixture from the first round was diluted 1:50, and a small portion of that dilution was used as the template for a second round of PCR using the nested primers. The results revealed an abundant product which matched the known deletion mutant gene in expected size between the ends determined by the primers. The product strands were easily visible on agarose gels at the expected size.

Three independent trials of the DNA sample from the pool known to contain the HY-4 deletion allele were conducted. In each instance the time for extension was limited in the first round of PCR and the product was then amplified in a second round of PCR with nested primers. All these trials resulted in the detection of the mutant in the second round products. By contrast, trials conducted in parallel using identical techniques with wild-type alleles only did not yield any mutant product.

ABI3 Gene

An *Arabidopsis thaliana* mutant named abi3-6 had been previously identified which contained an 800 base pair deletion in the ABI3 locus of its genome. (Nambara et al. Plant Cell Physiol. 35(3): 509–513 (1994)). An experiment was conducted to test if the existence of this deletion could be detected by this protocol within a pool of wild-type templates present at a ration of 1:1000 of mutant to wild-type.

Again four PCR primers were selected which would amplify both the wild-type and the deletion alleles. The primers were again intended to function as nested primers so that the outer set of primers were used for a first stage reaction while the internal set of primers were used in a second stage of amplification. The first primers would produce a product from the wild type template which would be 3053 base pairs in length while the same primers operating on the abi3-6 deletion mutant allele would produce a product of about 2.2 kb. The second primers were nested to produce a product on the wild-type template of 1029 base pairs and on the deletion mutant a product of about 200 base pairs.

Two separate DNA preparations were made. In one preparation, the DNA from only wild-type plants was used and in the second preparation, the DNA from the mutation was present. The two preparations were then mixed at a ration of 1:1000, wild-type to deletion mutant.

The first round of reactions were conducted using the same strategy as mentioned above with the HY-4 mutants. The parameters of the first round deletion enrichment PCR process is illustrated below in Table 3. The step A was done once. The steps B through D were repeated in sequence 51 times. Then step E was performed once.

TABLE 3

| A | 96° C. | 5 minutes | Start |
| B | 94° C. | 20 seconds | Denaturing |
| C | 65° C. | 1 second | Annealing |
| D | 72° C. | 5 seconds | Extension |
| E | 72° C. | 4 minutes | End |

Then the products from the first round were diluted as described for the HY-4 gene, and a second round of more standard PCR performed on the reaction products. The interior nested primers were used for this round. These primers were known to amplify the wild-type sequence and the deletion mutant sequence with equal efficiency. This round was conducted with the timing parameters set forth in Table 4. Step A was performed once and steps B through D were repeated in sequence 35 times.

TABLE 4

| A | 96° C. | 5 minutes | Start |
| B | 94° C. | 20 seconds | Denaturing |
| C | 65° C. | 10 seconds | Annealing |
| D | 72° C. | 4 minutes | Extension |

The reaction products from this second round were analyzed using agarose gel electrophoresis. An approximately 200 base pair PCR product was visible, which corresponds in size to the expected product from the abi3-6 deletion mutant. No such product was detected in parallel reactions conducted only with wild-type ABI3 genes present in the template solution. Using conventional PCR reactions, the presence of the mutant abi3-6 allele cannot be detected when it is present only at a ratio of 1:1000 in the template mixture.

We claim:

1. A method for identifying shorter target DNA sequences containing deletion mutations in a mixture of DNA strands which may contain the deletion mutant and which does contain multiple copies of non-mutant longer copies of the same target DNA sequence, the method comprising (a) denaturing the DNA strands by heating the mixture;
(b) cooling the mixture to permit primers to anneal to the strand of the denatured DNA strands, the primers selected to bind to the DNA strands of the target sequence whether or not the target DNA sequence contains a deletion mutation;
(c) selectively extending primers bound to deletion mutant DNA strands by performing a primer extension reaction with a DNA polymerase to extend the length of any primers which annealed to a target DNA sequence, one or more parameters of this extension step being altered to favor extension of the shorter deletion mutant versions of the target DNA sequence in preference over the creation of copies of the longer non-mutant versions of the target DNA sequence; and
(d) repeating steps (a) through (c) multiple time until multiple copies of the target DNA containing the deletion mutation are created.

2. A method as claimed in claim 1 wherein the parameter altered in step (c) is the time of the extension reaction.

3. A method as claimed in claim 1 wherein the parameter altered in step (c) is the temperature of the extension reaction.

4. A method as claimed in claim 1 wherein the parameter altered in step (c) is the addition of di-deoxy nucleotides into the extension reaction mixture.

5. A method for identifying shorter target DNA sequences containing deletion mutations in a mixture of DNA strands which may contain the deletion mutant and which does contain multiple copies of longer non-mutant copies of the same target DNA sequence, the method comprising the steps of:

(a) denaturing the DNA strands by heating the mixture;
(b) cooling the mixture to permit primers to anneal to the strand of the denatured DNA strands, the primers selected to bind to the DNA strands of the target sequence whether or not the target DNA sequence contains a deletion mutation;
(c) selectively extending primers bound to deletion mutant DNA strands by performing a primer extension reaction with a DNA polymerase to extend the length of any primers which annealed to a target DNA sequence, the time of this extension step being limited to a time sufficient so that extensions of the shorter deletion mutant version of the target sequence can be created but a time period too short for copies of the longer non-mutant versions of the target DNA sequence to be made; and
(d) repeating steps (a) through (c) multiple time until multiple copies of the target DNA containing the deletion mutation are created.

6. A method as claimed in claim 5 wherein the time period to which the extension reaction is limited is not more than about 14 seconds.

7. A method as claimed in claim 5 wherein the target DNA sequence is a plant gene and the mixture of DNA strands includes pooled DNA recovered from many plants of the same species.

8. A method as claimed in claim 5 further comprising the steps of taking the reaction products of the method of claim 5 and using those reaction products as the template in a conventional PCR reaction using primers that will binds to the deletion mutant version of the target sequence to make a quantity of copies of the mutant version of the target sequence which can be conveniently be detected.

* * * * *

UNITED STATES PATENT AND TRADEMARK OFFICE
CERTIFICATE OF CORRECTION

PATENT NO. : 6,358,690 B1
DATED : March 19, 2002
INVENTOR(S) : Patrick John Krysan and Michael Richard Sussman It is certified that error appears in the above-identified patent and that said Letters Patent is hereby corrected as shown below:

<u>Column 1,</u>
Line 7, please delete the entire paragraph and insert therefor the following:
-- This invention was made with United States government support awarded by the following agency:
USDA/CSREES: 95-37304-2364
The United States has certain rights in this invention. --

Signed and Sealed this

Seventh Day of October, 2003

JAMES E. ROGAN
*Director of the United States Patent and Trademark Office*